United States Patent
Mullen

[11] Patent Number: 6,120,447
[45] Date of Patent: Sep. 19, 2000

[54] ULTRASOUND IMAGE DATA WIRELESS TRANSMISSION TECHNIQUES

[75] Inventor: Paul Mullen, Waukesha, Wis.

[73] Assignee: General Electric Company, Milwaukee, Wis.

[21] Appl. No.: 09/224,454

[22] Filed: Dec. 31, 1998

[51] Int. Cl.[7] .................................................. A61B 8/00
[52] U.S. Cl. ........................................................ 600/437
[58] Field of Search ................................ 600/437, 443;
128/903, 904; 395/200.5, 200.53, 200.3,
200.31; 705/2, 3

[56] References Cited

U.S. PATENT DOCUMENTS

| | | | |
|---|---|---|---|
| 5,235,510 | 8/1993 | Yamoda et al. | 128/921 |
| 5,456,256 | 10/1995 | Schneider et al. | 600/459 |
| 5,603,323 | 2/1997 | Pflugrath et al. | 600/437 |
| 5,687,717 | 11/1997 | Halpein et al. | 128/903 |
| 5,715,823 | 2/1998 | Wood et al. | 600/437 |
| 5,758,649 | 6/1998 | Iwashita et al. | 600/459 |
| 5,778,177 | 7/1998 | Azor | 128/916 |
| 5,795,297 | 8/1998 | Doigle | 600/447 |
| 5,851,186 | 12/1998 | Wood et al. | 600/437 |
| 5,853,367 | 12/1998 | Chalek et al. | 600/437 |
| 5,867,821 | 2/1999 | Ballontyne et al. | 705/2 |
| 5,891,035 | 4/1999 | Wood et al. | 600/437 |
| 5,897,498 | 4/1999 | Confield, II et al. | 600/437 |
| 5,920,317 | 7/1999 | McDonald | 345/356 |
| 5,944,659 | 8/1999 | Floch et al. | 128/903 |
| 5,957,846 | 9/1999 | Chiang et al. | 600/447 |
| 6,006,191 | 12/1999 | Di Rienzo | 705/2 |
| 6,063,030 | 5/2000 | Vara et al. | 600/437 |

*Primary Examiner*—Francis J. Jaworski
*Attorney, Agent, or Firm*—McAndrews Held & Malloy; Christian G. Cabou; Phyllis Y. Price

[57] ABSTRACT

An ultrasound imaging system transmits data wirelessly by means of transmit and receive modules so that the data may be transferred to a network. Data also may be transmitted from the network wirelessly through modules to the ultrasound imaging system in order to control the system.

13 Claims, 1 Drawing Sheet

ULTRASOUND IMAGE DATA WIRELESS TRANSMISSION TECHNIQUES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to ultrasound imaging systems and more specifically relates to the transmission of data resulting from such systems.

Presently known ultrasound imaging systems generate image data which must be stored in a data base maintained in a storage device remote from the imaging system itself. The transmission of the data requires wires or cables which must be connected from the imaging system to the storage device.

Ultrasound imaging systems frequently are moved from bed to bed in a hospital ward. In such an environment, the wires required for data transmission become entangled in the beds or other equipment in the ward, and generally impede the progress of the ultrasound scanning. This invention solves these problems.

BRIEF SUMMARY OF THE INVENTION

This invention is useful in an ultrasound imaging system for generating image data in response to scanning of a subject under study. In order to implement the preferred embodiment of the invention, image data is generated by scanning a subject under study, preferably by operating an ultrasound imaging system. The image data is transmitted from a first location wirelessly using a network protocol. Preferably, the transmission is carried out by a network card and a network transmit module. The wirelessly transmitted image data is received at a second location different from the first location, preferably by a network receive module.

By using the foregoing techniques, image data may be generated by an ultrasound imaging system and may be transmitted without wires to a network. The network preferably is connected to a data image storage device. These techniques facilitate the movement of the ultrasound imaging system in a hospital ward and enable the ultrasound scanning to be carried out with a degree of convenience and efficiency previously unattainable.

DETAILED DESCRIPTION OF THE INVENTION

Figure 1:
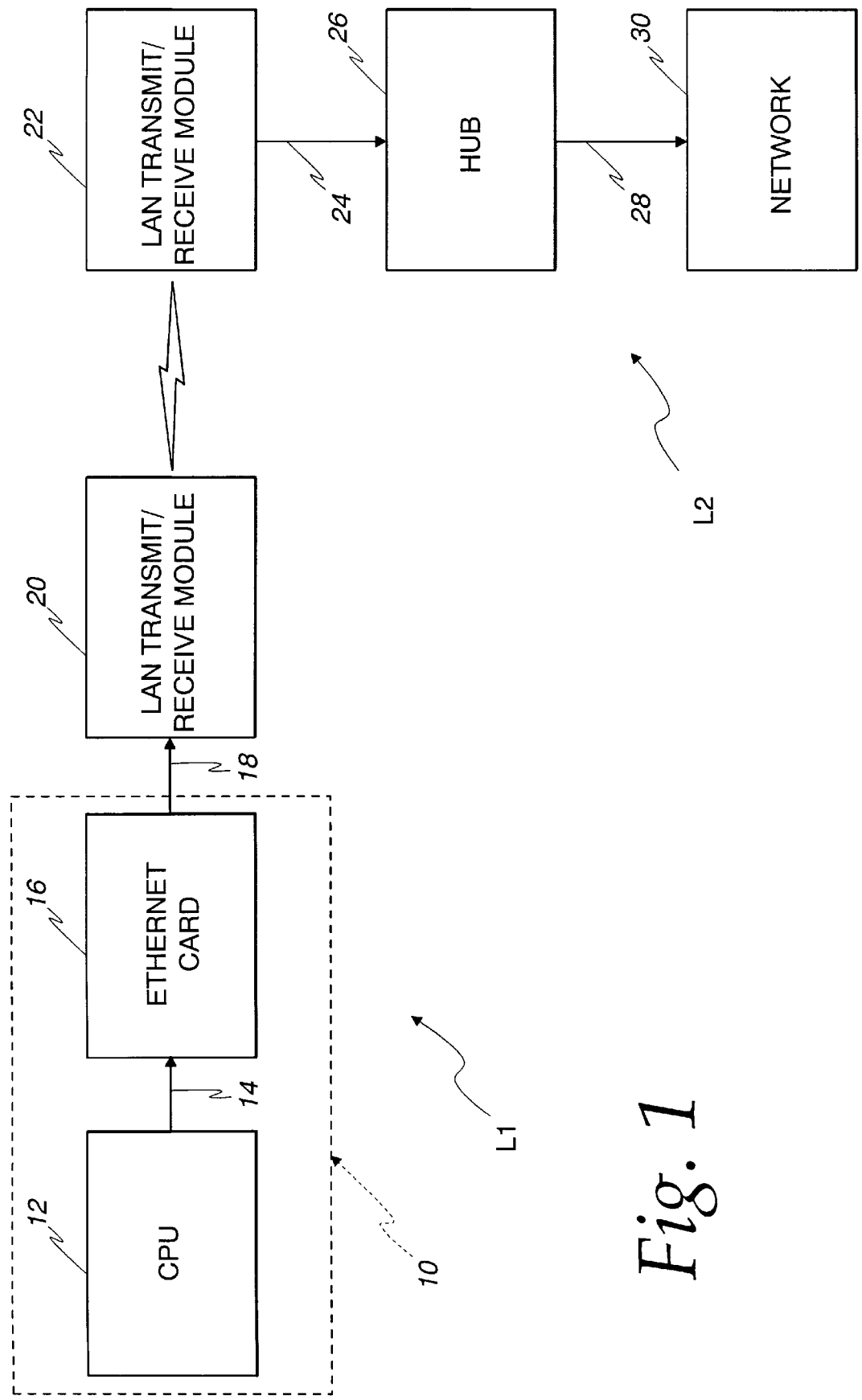
FIG. 1 is a schematic block diagram of a preferred embodiment of the present invention.

Referring to FIG. 1, a conventional ultrasound imaging system 10 is located in a location L1 and comprises a central processing unit 12 which communicates image data over a bus 14 to a local area network Ethernet card 16. The ultrasound scanning system may comprise, for example, the scanning systems bearing model numbers 700, 500 or 400 which are sold under the trademark LOGIQ by the Medical Systems Division of General Electric Company, Milwaukee, Wis. Such systems include a CPU 12 and an Ethernet network interface card 16 as shown in FIG. 1.

The image data is transmitted over a bus 18 to a conventional local area network transmit/receive module 20. Such modules are known to those skilled in the art. One exemplary module is model 364020-1 manufactured by AMP Corporation and sold under the trademark "Access Point 2". Module 20 transforms the image data into radio frequency signals which are transmitted wirelessly to a second location L2 and are received by another local area network transmit/receive module 22 which may identical to module 20.

The image data received at location L2 is transmitted over a bus 24 to a routing device, such as a HUB 26. The image data is then routed over a bus 28 to a network 30. Network 30 may be either an asynchronous network using the internet protocol or asynchronous network which transports ATM cells over conventional telephone switching equipment. Alternatively, network 30 may be a local area network connected to a data storage device capable of storing the image data.

Data received by network 30 may be transmitted through hub 26 and into module 22 and transmitted from module 22 to module 20. The receive data may be converted to the Ethernet protocol and transmitted to CPU 12 in order to help control system 10.

By using the foregoing techniques, image data may be transmitted wirelessly from imaging system 10 and data may be received wirelessly in order to provide control for imaging system 10.

Those skilled in the art will recognize that the preferred embodiment may be altered and modified without departing from the true spirit and scope of the invention as defined in the accompanying claims.

What is claimed is:

1. In an ultrasound imaging system for generating image data at a first location in response to scanning of a subject under study, improved apparatus for transmitting the data comprising in combination:

a computer connected to control the ultrasound imaging system;

a network interface connected to receive the image data from the computer;

a network transmit module coupled to the network interface connected to wirelessly transmit the image data before storage;

a network receive module connected to receive the wirelessly transmitted image data at a second location remote from the first location;

a routing device connected to route the received image data; and an asynchronous network for transmitting the received data via internet protocol, whereby image data generated by the ultrasound imaging system may be transmitted without wires to a network before storage.

2. Apparatus, as claimed in claim 1, wherein the network interface is a local area network interface.

3. Apparatus, as claimed in claim 1, wherein the network transmit module comprises a local area network transmit module.

4. Apparatus, as claimed in claim 1, wherein the network receive module comprises a local area network receive module.

5. Apparatus, as claimed in claim 1, and further comprising a routing module connected to route the image data to a network from the network receive module.

6. Apparatus, as claimed in claim 5, wherein the routing module comprises a hub.

7. Apparatus, as claimed in claim 1, wherein the network transmit module also comprises a network receive module.

8. Apparatus, as claimed in claim 1, wherein the network receive module also comprises a network transmit module.

9. In an ultrasound imaging system for generating image data at a first location in response to scanning of a subject under study, an improved method of transmitting the data comprising in combination:

generating image data by scanning a subject under study;

transmitting the image data wirelessly using a network protocol from the first location before storage;

receiving the wirelessly transmitted image data at a second location different from the first location;

asynchronously transmitting the received image data using internet protocol, whereby the image data may be routed to a network before storage.

10. A method, as claimed in claim 9, wherein the network protocol comprises a local area network protocol.

11. A method, as claimed in claim 9, wherein the network protocol comprises an Ethernet protocol.

12. A method, as claimed in claim 9, and further comprising the step of routing the image data to a network.

13. A method, as claimed in claim 9, and further comprising the step of receiving wirelessly transmitted data at the ultrasound imaging system.

\* \* \* \* \*